(12) United States Patent
Sprague et al.

(10) Patent No.: US 7,097,642 B1
(45) Date of Patent: Aug. 29, 2006

(54) CAUTERIZING SCALPEL BLADES

(75) Inventors: Robert T. Sprague, Crystal Lake, IL (US); Gavin P. Towler, Barrington, IL (US)

(73) Assignee: UOP LLC, Des Plaines, IL (US)

( * ) Notice: Subject to any disclaimer, the term of this patent is extended or adjusted under 35 U.S.C. 154(b) by 361 days.

(21) Appl. No.: 10/731,353

(22) Filed: Dec. 9, 2003

Related U.S. Application Data (63) Continuation-in-part of application No. 10/253,866, filed on Sep. 24, 2002, now Pat. No. 6,832,995, which is a continuation-in-part of application No. 10/200,794, filed on Jul. 22, 2002, now Pat. No. 6,824,555.

(51) Int. Cl.
*A61B 18/06* (2006.01)

(52) U.S. Cl. .......................... 606/27; 606/28

(58) Field of Classification Search ............ 607/27–28
See application file for complete search history.

(56) References Cited

U.S. PATENT DOCUMENTS

| | | | |
|---|---|---|---|
| 4,290,435 A | 9/1981 | Waggott | 128/800 |
| 4,627,435 A | 12/1986 | Hoskin | 128/303.1 |
| 4,679,561 A | 7/1987 | Doss | 128/422 |
| 4,737,628 A | 4/1988 | Lovoi | 250/226 |
| 4,796,622 A * | 1/1989 | Lu et al. | 606/28 |
| 4,872,458 A | 10/1989 | Kanehira et al. | 128/401 |
| 5,186,181 A | 2/1993 | Franconi et al. | 128/804 |
| 5,251,645 A | 10/1993 | Fenn | 607/154 |
| 5,324,299 A | 6/1994 | Davison et al. | 606/167 |
| 5,342,358 A * | 8/1994 | Daikuzono | 606/45 |
| 5,354,258 A | 10/1994 | Dory | 601/3 |
| 5,366,456 A | 11/1994 | Rink et al. | 606/16 |
| 5,528,561 A | 6/1996 | Castanis | 368/93 |
| 5,571,098 A | 11/1996 | Domankevitz et al. | 606/15 |
| 5,707,401 A | 1/1998 | Talmore | 607/88 |
| 5,776,175 A | 7/1998 | Eckhouse et al. | 607/100 |
| 6,051,005 A | 4/2000 | Brandsey et al. | 606/148 |
| 6,132,428 A | 10/2000 | VanDusseldorp | 606/46 |
| 6,159,200 A | 12/2000 | Verdura et al. | 606/1 |
| 6,165,184 A | 12/2000 | Verdura et al. | 606/148 |
| 6,235,037 B1 | 5/2001 | East et al. | 606/119 |
| 6,275,738 B1 | 8/2001 | Kasevich et al. | 607/101 |
| 6,312,435 B1 | 11/2001 | Wallace et al. | 606/130 |
| 6,337,998 B1 | 1/2002 | Behl et al. | 607/101 |
| 6,379,347 B1 | 4/2002 | Maki et al. | 606/17 |
| 6,383,179 B1 | 5/2002 | Neuberger | 606/16 |
| 6,394,998 B1 | 5/2002 | Wallace et al. | 606/1 |
| 6,416,524 B1 | 7/2002 | Critz et al. | 606/167 |
| 6,419,684 B1 | 7/2002 | Heisler et al. | 606/170 |

* cited by examiner

*Primary Examiner*—Henry M Johnson, III
(74) *Attorney, Agent, or Firm*—John G. Tolomei; Frank S. Molinaro; Arthur E. Gooding (57) ABSTRACT

An apparatus is disclosed for cutting and cauterizing of tissue. The apparatus comprises a cutting edge of a blade. The apparatus further comprises a conduit having a catalyst located near the conduit outlet, and the conduit is for delivering a combustible mixture of gases. The gases react in the presence of the catalyst and generate heat. The heat generated cauterizes blood vessels when applied to the cut tissue.

21 Claims, 6 Drawing Sheets

CAUTERIZING SCALPEL BLADES

CROSS-REFERENCE TO RELATED APPLICATIONS

This application is a Continuation-In-Part of U.S. application Ser. No. 10/253,866, filed Sep. 24, 2002, now U.S. Pat. No. 6,832,995, which is a Continuation-In-Part of U.S. application Ser. No. 10/200,794, filed Jul. 22, 2002, now U.S. Pat. No. 6,824,555, all of which are incorporated by reference.

FIELD OF THE INVENTION

The present invention relates to surgical cutting instruments. In particular, this invention relates to scalpels that incorporate means for cauterizing blood vessels during usage of the scalpel.

BACKGROUND OF THE INVENTION

Surgical operations often involve the cutting of a patient's tissue. Usually, the tissue is cut with a scalpel, a sharp edged cutting instrument. However, the cutting of a patient's tissue is also usually accompanied by an undesired flow of blood from small blood vessels within the tissue. Reducing, or eliminating this blood flow is advantageous to the patient by reducing blood loss and to the surgeon by removing or reducing an obstruction to the surgeon's view of the incised tissue.

Scalpels making use of lasers for heat sources can be used to heat and irradiate the incised tissue. Light of an appropriate wavelength is absorbed by the tissue, and the optical energy is converted to thermal energy to cauterize the tissue. Cutting instruments of this type are described in U.S. Pat. Nos. 6,383,179; 5,571,098; 5,366,456; and 4,627,435. These devices can use the laser to incise the tissue as well as cauterize, or use an optically transparent material for the cutting instrument coupled with a bundle of optical fibers for directing the laser to the area of interest.

Another method of providing cauterizing heat with a scalpel is the use of ultrasonics. U.S. Pat. No. 5,324,299 describes such a device wherein the scalpel blade is vibrated at a rate around 55,000 cycles per second. The vibration generates ultrasound waves for heating the tissue, however, there is only limited cauterizing ability.

Control of blood loss can be achieved by cauterizing the small blood vessels in the tissue at the time the tissue is cut. Cauterization of the blood vessels is achieved by applying heat at the vessels. It is advantageous to apply the heat at the time the tissue is cut and at the tissue without exposing the tissue to radiation.

SUMMARY OF THE INVENTION

The present invention provides a device for cauterizing tissue during the process of cutting the tissue. The apparatus comprises a blade having a cutting edge. The apparatus further includes a conduit, or needle, having an inlet, an outlet, and a predetermined orientation relative to the blade. The apparatus further includes a catalyst disposed proximate to the outlet end of the conduit. This invention provides a convenient heat source that can be positioned proximate to the cut tissue as the tissue is being cut by the blade.

In one embodiment, the invention includes a scalpel blade having a cutting edge with a means for attachment to a handle. The blade comprises at least one channel formed therein with each channel having an inlet end and an outlet end. The outlet end of each channel is positioned proximate to the cutting edge of the blade. The apparatus includes a catalyst disposed proximate to the outlet end of each channel. The invention provides a means to heat the scalpel blade through reaction of a gas mixture flowing over a catalyst and cauterizing capillaries cut when tissue is cut.

In another embodiment, the invention includes a handle and a first scalpel blade having a cutting edge with a means for attachment to the handle. The invention further includes a second blade with a means for attachment to the handle. The second blade has a leading edge in a predetermined position relative to the cutting edge of the first blade. The second blade includes at least one channel formed therein with each channel having an inlet end and an outlet end. The outlet end of each channel is positioned proximate to the leading edge of the second blade. The apparatus further includes a catalyst disposed proximate to the outlet end of each channel. The invention provides a means to cauterize capillaries when the tissue is cut by the first blade.

Other objects, advantages and applications of the present invention will become apparent to those skilled in the art from the following detailed description.

Additional objects, embodiments and details of this invention can be obtained from the following detailed description of the invention.

BRIEF DESCRIPTION OF THE DRAWINGS

FIG. 3b is a cross sectional view of the second variation showing two needles with the blade;

DETAILED DESCRIPTION OF THE INVENTION

Surgical procedures usually require the cutting of a patient's tissue. However, accompanied with the tissue cutting is the flow of blood from the network of small capillaries in the tissue. The blood obstructs the surgeon's view, and the open capillaries present sites for possible entry of infection, as well as requiring blood replacement if the bleeding is excessive. Cauterizing the capillaries as they are cut will reduce the amount of blood flowing into the region of the cut, and will reduce the risk of infection by closing the ends of the capillaries. Cauterizing seals by applying heat to the site and by applying heat during the cutting process, the capillaries are closed as they are cut. The present invention is a scalpel blade that provides heat for cauterizing capillaries as they are cut.

Figure 1:
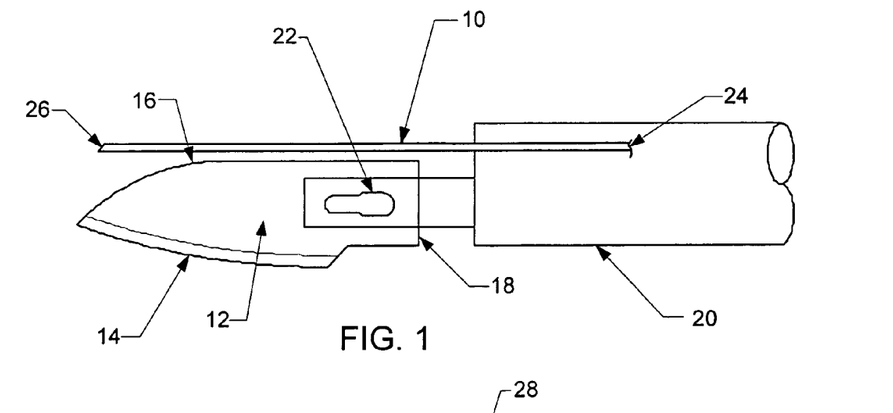
FIG. 1 is an embodiment of the invention showing a scalpel with a needle for providing heat to cauterize blood vessels.

A first embodiment of the present invention, as shown in FIG. 1, comprises a conduit in the form of a needle 10 in close proximity to a scalpel blade 12. The blade 12 has a cutting edge 14, a non-cutting edge 16, and an edge 18 distal to the cutting edge 14. The embodiment includes a handle 20 and a means 22 for releasably attaching the blade 12. The needle 10 has an inlet 24 and an outlet 26, and is affixed to the handle 20 in a manner such that the outlet 26 is in a predetermined position relative to the blade 12. The needle further includes a catalyst disposed near the needle outlet 26. This embodiment positions the source of heat near the non-cutting edge 16 of the scalpel blade 12. The needle 10 has an inner diameter of less than 400 micrometers with the inner diameter preferably about 200 micrometers. As used hereinafter, the term needle will mean a conduit of any form that meets the limitations on the inner diameter.

A gas mixture flows from a conduit inlet 24 through the conduit 10 and flows over the catalyst proximate to the outlet 26 of the conduit. The gas mixture reacts when flowing over the catalyst and generates heat. The choice of chemicals in the gas mixture is dependent on the application. For use in a medical procedure, the preferred gas mixture is one of hydrogen and oxygen. The mixture preferably has a molar ratio of hydrogen to oxygen of about 2 to 1, or slightly less, for the combustion of hydrogen and oxygen in this ratio generates water with no waste products or excess gas. The gas mixture can be generated in a variety of ways. One method of generating the mixture is to provide individual gas cylinders, meter the flow of gases from the cylinders and mix the gases using a mixer. Another method, usable for generating a hydrogen and oxygen mixture, is to use electrolysis. The flow of gas is generated in a stoichiometric ratio and can be controlled through the rate of usage of electrical power. For gases, such as hydrogen and oxygen, the gases are mixed in a micromixer and flow through a narrow tube to the conduit inlet 24.

In a variation of the first embodiment, the needle is packed with an inert porous media providing for average channel diameters of less than 200 micrometers. This allows for larger conduits having initially larger channel diameters. The larger diameter channels are reduced to a series of interconnected channels having smaller channel diameters. In addition, this allows for the option of a plurality of smaller diameter channels bundled together wherein each smaller channel has a diameter of less than 200 micrometers, and the bundle permits greater flow of the gas mixture. Near the tip of the needle, the inert porous media is coated with an appropriate catalyst to initiate a reaction between the reactants. In particular, the reactants are oxygen and hydrogen gas. The reactants preferably have a stoichiometric ratio for a combustion reaction producing water, or a mixture that is slightly rich in oxygen.

Figure 2:
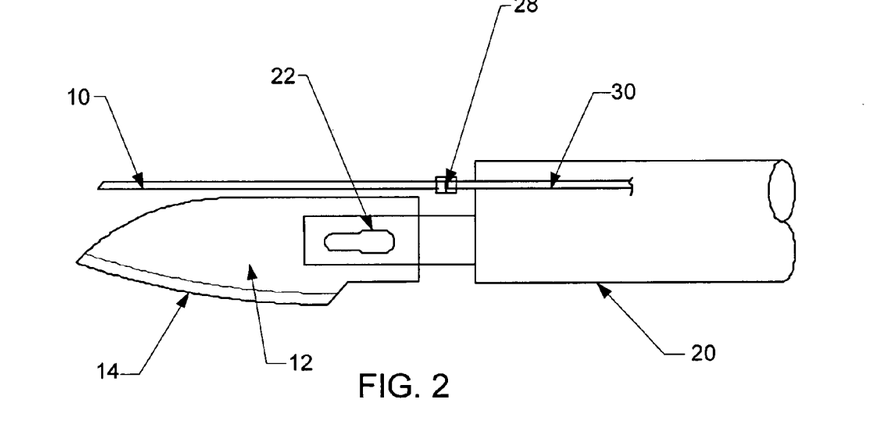
FIG. 2 is a second embodiment of the invention.

In an alternate, or second, embodiment, as shown in FIG. 2, the apparatus further includes a releasable attachment means 28. This allows for the use of disposable needles while retaining a reusable handle 20. The attachment means 28 include, but are not limited to, gas type fittings such as a miniature compression fitting or luer type fitting. The handle 20 includes a supply capillary 30 for delivering a mixture of gas to the inlet 24 of the needle 10. The capillary 30 has an inner diameter less than 400 micrometers, and preferably an inner diameter of about 200 micrometers. The inner diameter is sized to permit smooth flow of the gas mixture, but to be sized sufficiently small to prevent any propagation of the reaction along the length of the capillary 30, or the length of the needle 10.

Figure 3A:
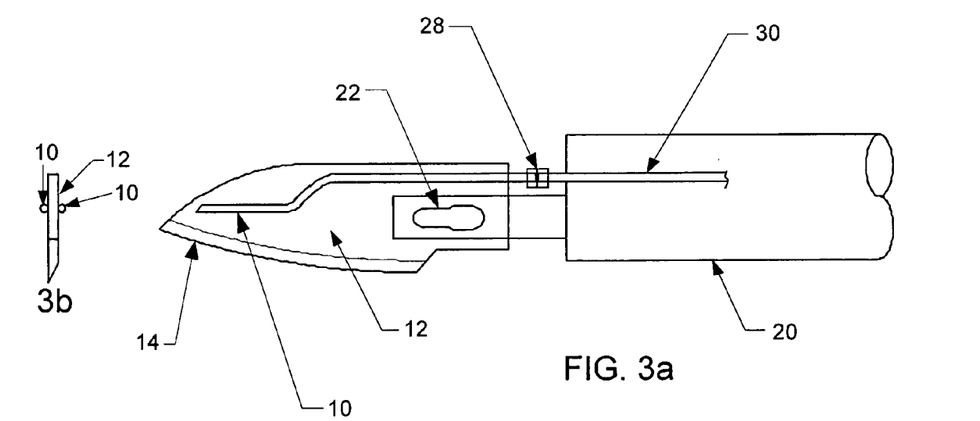
FIG. 3a is a variation of the second embodiment of the invention showing two needles for providing heat.

The present invention also allows for multiple conduits attached in proximity to the cutting blade. In FIGS. 3a and b, the apparatus is shown with a blade 12 and two needles 10, with a needle 10 disposed on each side of the blade 12. The needles 10 can be releasably attached to the handle 20 either separately, or as a single unit.

Figure 4:
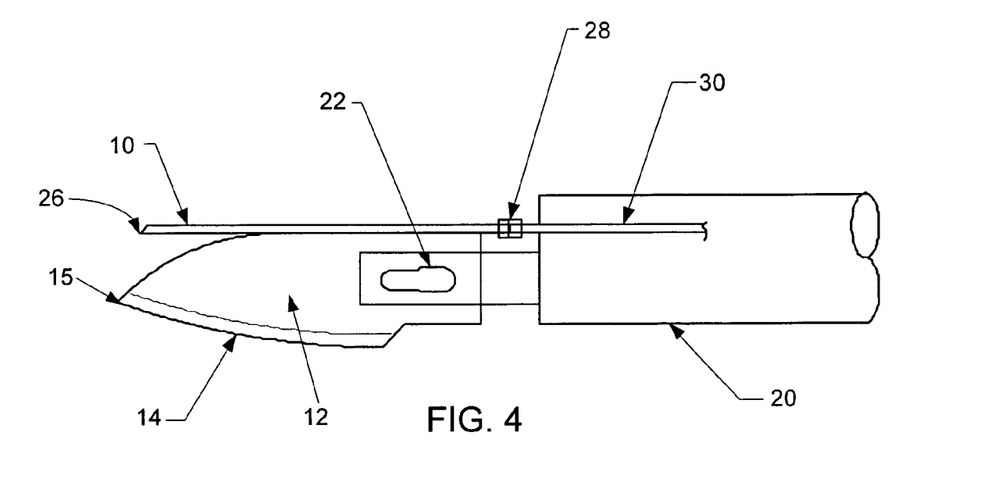
FIG. 4 is a third embodiment of the invention with the needle affixed to the blade.
Figure 5:
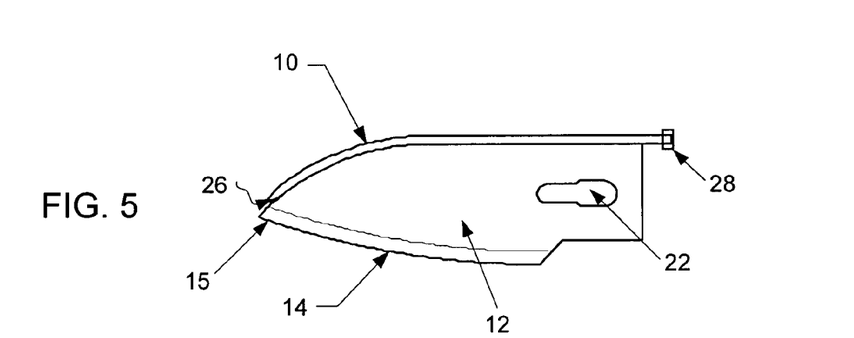
FIG. 5 is a variation of the third embodiment with the needle affixed to the blade and the needle tip positioned near the tip of the blade.
Figure 6:
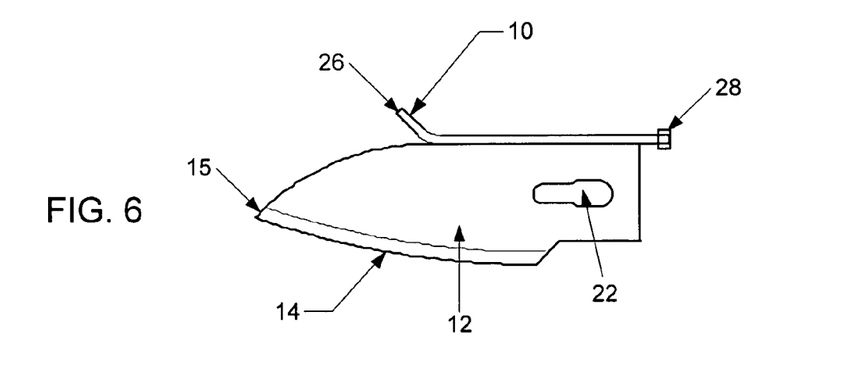
FIG. 6 is a second variation of the third embodiment with the needle affixed to the blade and the needle tip positioned away from the blade.

FIGS. 4, 5, and 6 show various configurations for a third embodiment of the needle 10 relative to the blade 12. The needle 10 can be affixed to the blade 12 for further rigidity in holding the needle 10 in a fixed orientation relative to the blade 12, creating a needle-blade assembly. In this embodiment, a portion of the needle 10 is affixed along the non-cutting edge of the blade 12, allowing for the outlet 26 of the needle to be positioned either near the tip 15 of the blade as in FIG. 5, or away from the tip 15 as in FIG. 6. The needle-blade assembly is releasably attached to the handle 20 via two connections, a blade mount 22 and a needle fitting 28. The needle 10 can be affixed to the blade 12 by any suitable process, and includes welding, brazing, soldering, and adhesives. As shown in the FIGS. 4–6, the needle 10 is bent or straight to provide heat release at the tip 15 of the blade 12, or at some position removed from the cutting edge 14. The use of a needle 10 with the heat release at the blade tip 15 provides for concomitant cauterization with the cutting of tissue. If the area to be cauterized is away from the blade tip 15, then a blade-needle combination having the needle tip 26 away from the blade tip 15 is used, for example when cutting through skin, the blood vessels in the skin might need to be cauterized without cauterizing underlying tissue.

Figure 7:
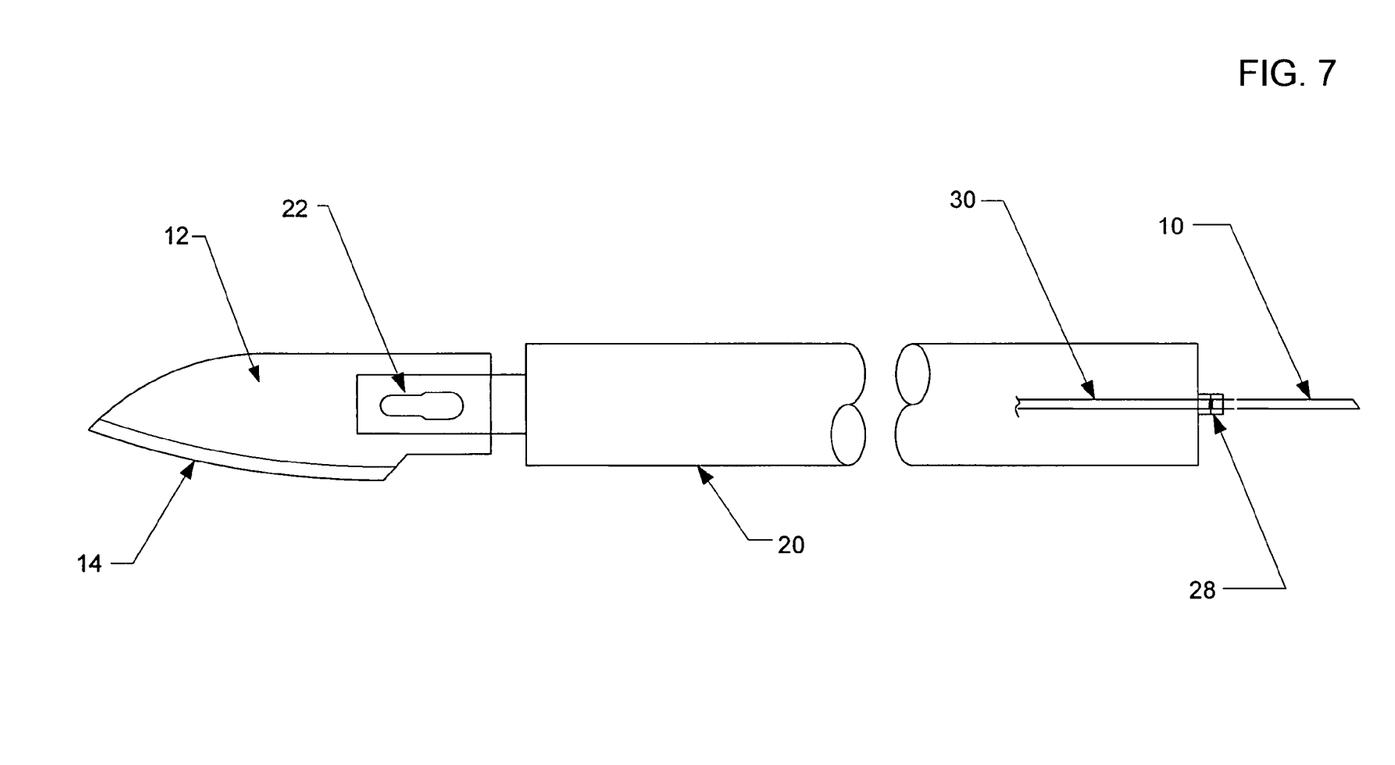
FIG. 7 is a variation of the first embodiment with the needle at an opposing position on the handle relative to the blade.

The use of a heat source in medical procedures is not always concomitant, but can often be useful to have handy during a procedure. To that end, an embodiment that places the device in a convenient position for a surgeon is shown in FIG. 7. The needle 10 is attached to the handle 20 at a position opposite the blade 12 which allows the surgeon to turn the handle 20 around and use the cauterizing needle 10 when desired. The apparatus comprises a handle 20 for holding a blade 12. The apparatus includes a means 22 to releasably attach the blade 12 to the handle 20. The apparatus further includes a conduit 30 as a part of the handle 20. The conduit 30 is preferably positioned within the handle 20 and terminates at the opposite end of the handle 20 from the blade attachment means 22. A needle 10 is releasably attached to the handle 20 through a needles attachment means 28. there are numerous designs that provide for a needle attached to a scalpel handle with the needle in a convenient position, but away from the blade. It is intended that this design cover those alternate designs which are too numerous to enumerate here. In addition, operation of the needle can be controlled through a switch for controlling flow of gas over the catalyst. The inclusion of a flow control switch is a preferred feature for all the embodiments of the present invention. In this embodiment, the inlet to the conduit 30 is in a position in the middle of the handle 20. Preferably, the inlet has means for releasable attachment to a tube delivering the gas mixture to the conduit 30.

Alternate designs for a cutting blade with the capability to apply heat to the tissue cut include specialty designs. One such specialty design includes incorporating the channels for carrying a gas mixture as an integral part of the cutting blade. The blades are formed of two plates of a material that is later bonded together to form the blade. Into one of the plates, grooves are cut and with the bonding of the second plate over the grooves channels are formed within the blade. The grooves are cut using methods known in the art for producing small grooves, and include, but are not limited to, chemical etching, and micro-machining. The grooves are formed with a diameter of less than 400 micrometers, and preferably with a diameter of about 200 micrometers. After formation of the grooves, the plates are joined together forming the blade and channels within the blade. The plates are joined using techniques known in the art and include, but are not limited to, diffusion bonding. Following the joining of the plates to form a blade, the blade is machined to form a cutting edge from one of the edges of the blade.

The blades 12 of the present invention maybe made of any hard material capable of having a sharp edge formed. Materials include metals, such as stainless steels, ceramics, glasses, quartz, thermoset plastics, and alloys of metals.

Figure 8:
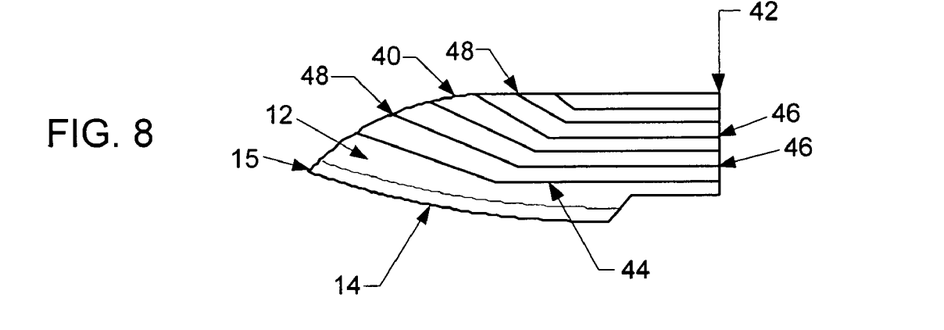
FIG. 8 is an embodiment of a cauterizing scalpel blade with channels terminating near the non-cutting edge of the blade.

The grooves are cut in a pattern to distribute the outlets of channels along the non-cutting edge of the blade. One such pattern is shown in FIG. 8. The blade 12 has a cutting edge 14, a non-cutting edge 40, and a distal edge 42. The blade 12 includes at least one channel 44 defined therein, and formed as described above. The channels 44 have an inlet 46 in fluid communication with a source of gas mixture and positioned near the distal edge 42 of the blade, and an outlet 48 positioned near the non-cutting edge 40. A catalyst is deposited on the blade 12 near the outlets 48 of the channels 44. Preferably, the catalyst is deposited in the channels 44 near the channel outlets 48. This can be performed by depositing the catalyst within the groove at the desired location prior to the bonding of the two plates.

Figure 9:
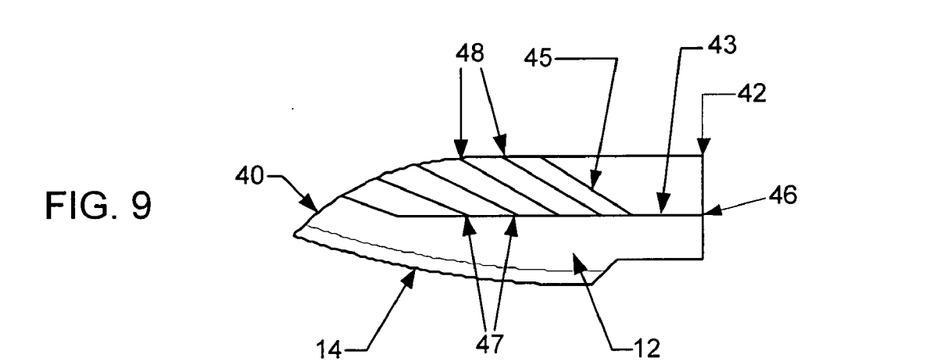
FIG. 9 is a variation of the embodiment of a cauterizing scalpel blade with channels terminating near the non-cutting edge of the blade.

A second variation of this embodiment is shown in FIG. 9. The blade 12 includes a main channel 43 having an inlet 46 positioned near the distal edge 42 of the blade 12 and in fluid communication with a source of gas mixture. The blade 12 further includes a plurality of secondary channels 45, with each channel 45 having an outlet 48 positioned near the non-cutting edge 40 of the blade, and an inlet 47 terminating at the main channel 43.

Figure 10:
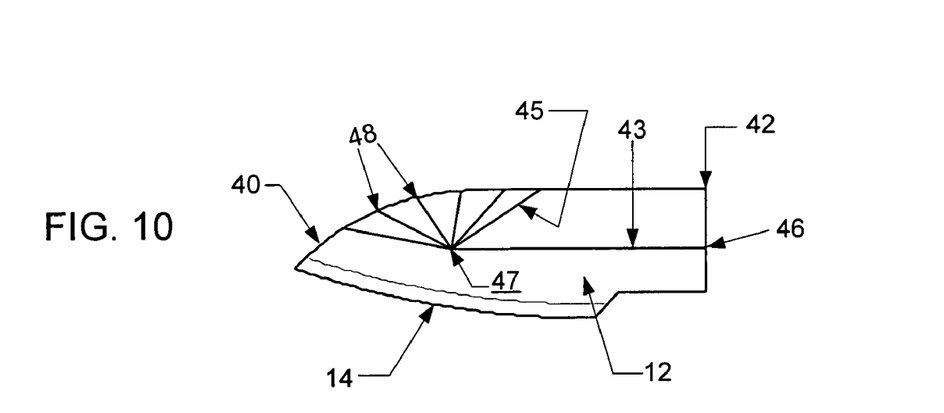
FIG. 10 is a second variation of the embodiment of a cauterizing scalpel blade with channels terminating near the non-cutting edge of the blade.

A third variation is shown in FIG. 10. The blade 12 includes a main channel 43 with an inlet 46 near the distal end 42 of the blade 12, and an outlet. A plurality of secondary channels 45 are formed in the blade 12 radiating out from the main channel outlet, with the secondary channel inlets 47 intersecting the main channel 43 outlet, and the secondary channel outlets 48 terminating near the non-cutting edge 40 of the blade 12.

The channels 44 of the first variation, or the secondary channels 45 of the second and third variations can be sized to control distribution of the gas mixture to the outlets 48. For providing more heat near the tip 15 of the cutting blade, either more secondary channels 45, or larger secondary channels 45 are formed in the blade terminating near the tip. The number, size, and distribution of channels 44 and secondary channels 45 are set according to the needs of a particular type of operation. Embodiments of the invention include a blade with a uniform distribution of secondary channel outlets 48 along the non-cutting edge 40 of the blade; a blade with a uniform distribution of secondary channel outlets 48 near the tip of the blade along the non-cutting edge 48; and a blade with a non-uniform distribution of secondary outlets 48 along the non-cutting edge 48 of the blade. The last embodiment provides for multiple regions of selective heating along the blade 12.

Figure 11:
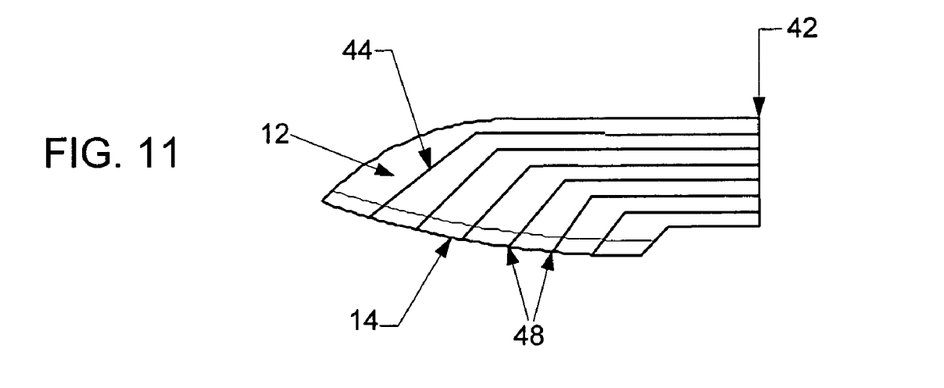
FIG. 11 is an embodiment of a cauterizing scalpel blade with channels terminating near the cutting edge of the blade.
Figure 12:
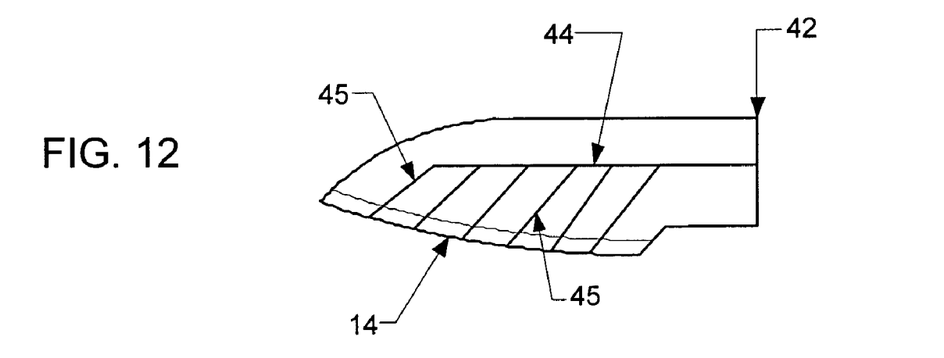
FIG. 12 is a variation of the embodiment of a cauterizing scalpel blade with channels terminating near the non-cutting edge of the blade.
Figure 13:
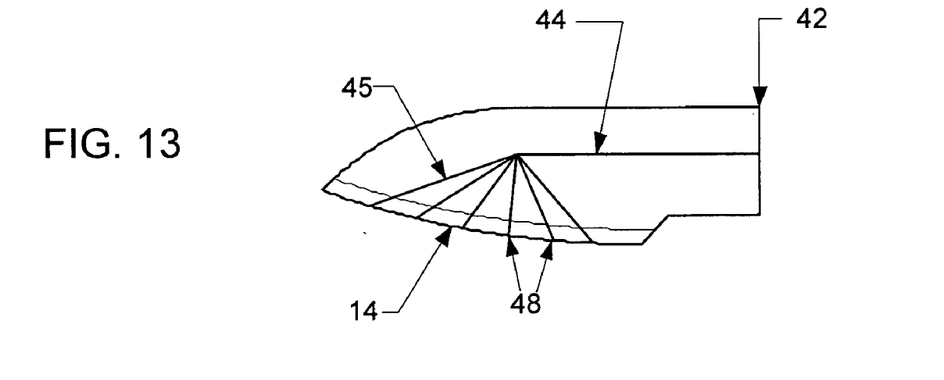
FIG. 13 is a second variation of the embodiment of a cauterizing scalpel blade with channels terminating near the non-cutting edge of the blade.

For providing heat immediately upon cutting tissue, and thereby cauterizing the cut blood vessels nearly simultaneously with the cutting of the tissue, the blade 12 is heated at the cutting edge 14. FIGS. 11 to 13 show several configurations of a scalpel blade having channels formed within the blade 12, but with the channels 44 or the secondary channels 45 terminating at the cutting edge 14. These designs are formed as the above described scalpel blades having the channels 44 or the secondary channels 45 terminating at the non-cutting edge 40 of the blade 12. A catalyst is disposed at the outlets 48 positioned near the cutting edge 40.

Figures 14A, 14B:
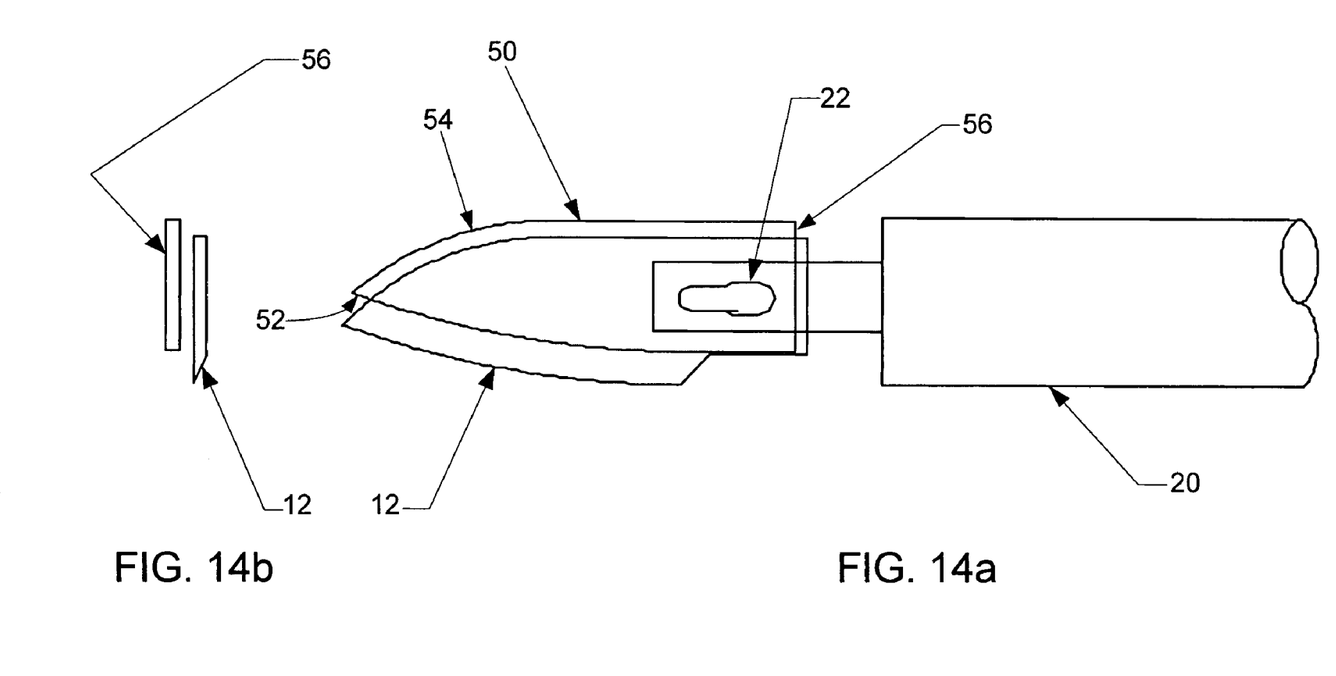
FIG. 14a is an embodiment of the present invention wherein the cauterizing scalpel has two blades.
FIG. 14b is a cross sectional view of the two blade embodiment.

In yet another embodiment, a cutting blade is used in conjunction with a non-cutting blade, as shown in FIGS. 14a and 14b. This embodiment provides for the ability to separate the tissue before cauterizing, or for selectively cauterizing blood vessels on one side of an incision. A first blade 12 is for cutting tissue, and as the tissue is cut, and a second blade 50 contacts the cut tissue. The second blade 50 is in a substantially parallel orientation relative to the cutting blade 12, but is positioned to follow the cutting blade 12 as the cutting blade 12 moves to cut tissue. The second blade 50 contacts the cut tissue and cauterizes the cut capillaries in the tissue, and can be positioned to separate the cut tissue to a desired spacing. The second blade 50 has a leading edge 52, an edge opposite the leading edge 54, and a distal edge 56, and includes at least one channel 44 defined therein, and formed as described above. The channel 44 has an outlet 48 positioned near the leading edge 52, and an inlet 46 positioned near the distal edge 56 of the second blade 50. The inlet 46 is in fluid communication with a source of gas mixture. A catalyst is deposited on the blade 50 proximate to the channel outlet 48. Preferably, the catalyst is deposited in the channel near the channel outlet 48, and this can be performed by depositing the catalyst within the groove at the desired location prior to the bonding of the two plates. In an alternate embodiment, the channel outlet 48 is positioned near the edge opposite the leading edge 54.

Alternate embodiments of the second blade 50 include embodiments with a plurality of channels 44 formed therein, a plurality of secondary channels in fluid communication with main channels, and equivalent designs as described above for the first blade 12. Also, additional embodiments include having the first and second blades 12, 50 with channels formed therein.

While the invention has been described with what are presently considered the preferred embodiments, it is to be understood that the invention is not limited to the disclosed embodiments, but is intended to cover various modifications and equivalent arrangements included with the scope of the appended claims.

What is claimed is:

1. An apparatus for cutting comprising:
   a blade having a cutting edge, and a means of attachment to a handle assembly;
   a conduit having an inlet, an outlet, and a predetermined orientation relative to the blade; and a catalyst disposed proximate to the conduit outlet.

2. The apparatus of claim 1 wherein the blade has a tip and the conduit outlet is disposed proximate to the blade tip.

3. The apparatus of claim 1 further comprising;
a second conduit having an inlet, an outlet, and a predetermined orientation relative to the blade; and
a catalyst disposed proximate to the second conduit outlet.

4. The apparatus of claim 3 wherein the blade has a first side and a second side, and the second conduit is disposed on the second side of the blade.

5. The apparatus of claim 3 wherein the second conduit is disposed on the same side of the blade as the first conduit.

6. The apparatus of claim 1 further comprising; a handle assembly having a handle conduit, said handle conduit having an inlet and an outlet, wherein the handle conduit outlet releasably attaches to the conduit inlet, and is in fluid communication with the conduit inlet.

7. The apparatus of claim 1 wherein the catalyst comprises a catalytic metal wherein the catalytic metal comprises at least one metal selected from the group consisting of scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), gallium (Ga), germanium (Ge), indium (In), thallium (Ti), tin (Sn), lead (Pb), antimony (Sb), bismuth (Bi), polonium (Po), and mixtures thereof.

8. The apparatus of claim 7 wherein the catalytic metal comprises at least one metal selected from the group consisting of platinum, palladium, rhenium, rhodium, nickel, iron, and mixtures thereof.

9. The apparatus of claim 1 wherein the blade is made of a material selected from the group consisting of stainless steels, ceramics, glasses, quartz, thermoset plastics, and alloys of metals.

10. The apparatus of claim 1 wherein the conduit has an internal diameter of less than 400 micrometers.

11. A scalpel blade for cutting tissue comprising:
a blade comprising a cutting edge, a non-cutting opposing edge, an edge distal to the cutting edge, and a means for attachment to a handle, and defining at least one channel therein, wherein the channel has an inlet proximate to the distal edge, and an outlet proximate to the non-cutting edge; and
a catalyst disposed proximate to the channel outlet.

12. The scalpel blade of claim 11 wherein the blade defines a plurality of channels, wherein each channel has an inlet proximate to the distal edge, and an outlet proximate to the non-cutting edge.

13. The scalpel blade of claim 11 wherein the blade defines a main channel and a plurality of secondary channels, and wherein the main channel has an inlet proximate to the distal edge, the secondary channels are in fluid communication with the main channel, and the secondary channels each have an outlet proximate to the non-cutting edge.

14. The scalpel blade of claim 13 wherein the plurality of secondary channel outlets are distributed uniformly along the non-cutting edge.

15. The scalpel blade of claim 13 wherein the plurality of secondary channel outlets are distributed uniformly near the tip of the blade along the non-cutting edge.

16. The scalpel blade of claim 13 wherein each secondary channel has an inlet proximate to the main channel outlet.

17. The scalpel blade of claim 13 wherein the secondary channel outlets are distributed along the non-cutting edge in a non-uniform distribution for directed local heating of the scalpel blade.

18. The scalpel blade of claim 11 wherein the catalyst comprises a catalytic metal wherein the catalytic metal comprises at least one metal selected from the group consisting of scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), gallium (Ga), germanium (Ge), indium (In), thallium (Tl), tin (Sn), lead (Pb), antimony (Sb), bismuth (Bi), polonium (Po), and mixtures thereof.

19. A scalpel for cutting tissue and cauterizing blood vessels comprising:
a handle with at least two attachment means for blades;
a first blade having a cutting edge, a non-cutting opposing edge, and a distal edge proximate to a means for attachment to the handle;
at least one second blade with a means for attachment to the handle and defining at least one channel therein, with an inlet and an outlet; and
a catalyst disposed proximate to the channel outlet.

20. The scalpel of claim 19 wherein the first blade further defines at least one channel therein, with an inlet and an outlet; and
a catalyst disposed proximate to the channel outlet.

21. An apparatus for cutting comprising:
a handle assembly having a blade attachment end, an end distal the blade attachment end, and a conduit with the conduit outlet proximate the distal end;
a blade having a cutting edge and a means of attachment to the handle assembly;
a conduit having an inlet in fluid communication with the handle assembly conduit outlet, and an outlet; and
a catalyst disposed proximate to the conduit outlet.

* * * * *